US00PP18173P2

(12) United States Plant Patent
Egger

(10) Patent No.: US PP18,173 P2
(45) Date of Patent: Oct. 30, 2007

(54) ***HEUCHERA* PLANT NAMED 'GINGER ALE'**

(50) Latin Name: ***Heuchera* spp.**
Varietal Denomination: Ginger Ale

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 5 days.

(21) Appl. No.: 11/452,679

(22) Filed: Jun. 13, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—Annette H Para
(74) *Attorney, Agent, or Firm*—Klarquist Sparkman, LLP

(57) ABSTRACT

A new and distinct hybrid of *Heuchera* plant characterized by lightly veiled, pale ale colored foliage and creamy yellow colored flowers on reddish peduncles, and excellent vigor.

1 Drawing Sheet

Botanical Denomination: *Heuchera* spp.
Variety Designation: 'Ginger Ale'.

The present invention relates to a new and distinct cultivar of *Heuchera* hybrid and given the cultivar name of 'Ginger Ale'. *Heuchera* is in the family *Saxifragaceae. Heuchera* 'Ginger Ale' originated from a cross between *Heuchera* 44-1, a proprietary non commercial plant, as the seed parent, and *Heuchera* 148-1, a proprietary non commercial plant, as the pollen parent. Given its ornamental foliage and flower form it is probable that *Heuchera americana, H. sanguinea,* and *H. brizoides* are in its parentage.

This new *Heuchera* is distinguished by:

1. Lightly veiled, pale ale colored foliage.
2. Creamy yellow colored flowers on reddish peduncles.
3. Excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg. shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWING

The drawing shows a two-year-old plant of *Heuchera* 'Ginger Ale' growing in the ground in full sun in the trial field in May in Canby, Oreg.

DETAILED PLANT DESCRIPTION

The following is a detailed description of the new *Heuchera* cultivar based on observations taken in May of a three-year-old specimen grown a two gallon container in an open air shade house with 50% shade cover and added irrigation in the summer months in Canby, Oreg. Canby is Zone 8 on the USDA Hardiness map. Temperatures range from a high of 95 degrees F. in August to and average of 32 degrees F. in January. Normal rainfall in Canby is 42.8 inches per year. The color descriptions are all based on The Royal Horticultural Society Colour Chart.

Plant:

*Form.*—Basal rosette, herbaceous perennial.
*Hardiness.*—USDA Zone 4 to 9.
*Size.*—13 cm tall from the ground to the top of the foliage and 45 cm wide.
*Habit.*—Mounding.
*Vigor.*—Excellent.
*Roots.*—Fibrous, freely branching, fine, and white in color. Roots develop easily from cuttings.

Leaf:

*Type.*—Simple.
*Arrangement.*—Rosette.
*Shape.*—Ovate.
*Lobing/division.*—5 main lobes, each with one or two secondary lobes.
*Venation.*—Palmate.
*Margins.*—Crenate.
*Apex.*—Mucronulate.
*Base.*—Cordate, lobes overlapping at the base, one side curling up.
*Blade size.*—7 to 10 cm long and 6.5 to 8.5 cm wide.
*Surface texture.*—Glandular on both sides.
*Petiole description.*—10 to 17 cm long and 2 mm wide, strongly pubescent, color is Greyed Orange 174A.
*Leaf color.*—Top side — New growth is Greyed Brown 199A with a strong white veil over the top, Greyed White 156C. Mature leaves are Yellow Green 152B with the veil, Greyed White 156C. In sun these bleach to Yellow 2D. Winter leaves are Yellow Green 152A on the veins, Greyed White 156D on the veils, and Greyed Purple 187B on the margins. Bottom side — Between Greyed Purple 183C and Red Purple 59A.

Inflorescence:

*Type.*—Thyrse.
*Number of flowers.*—60 to 70 per thyrse.
*Number of thyrse in spring.*—50.

*Peduncle.*—With 0 to 1 cauline leaf, grows to 47 cm tall and 3 mm wide at the base, Greyed Purple 187B, glandular hairs.

*Pedicel.*—Variable in length, Greyed Purple 187B, glandular hairs.

*Bloom period.*—May in Canby, Oreg.

Flower Bud:

*Size.*—3 mm wide and 5 mm long.

*Description.*—Glandular, ovoid.

*Color.*—Yellow 10C on the top half and Greyed Red 179B on the bottom half.

Flower:

*Type.*—Perfect, zygomorphic.

*Shape.*—Campanulate.

*Size.*—7 mm long and 5 mm wide.

*Petal description.*—5 inconspicuous, White 155A on both sides, 1.3 mm wide and 3 mm long, tip acute, margin entire, glandular on backs.

*Calyx description.*—5 lobes, divided ⅓ way to the base, glandular inside and out, tips acute, margin entire, reflexed, 7 mm long and 5 mm wide.

*Calyx and overall flower color.*—Yellow 10D darkening to Greyed Red 179B past maturity on both sides.

*Stamen description.*—5, filaments White 155A and 2.2 mm long, anthers 1 mm with pollen Orange 25A.

*Pistil description.*—6 mm long, Green Yellow 1D at the ovary to white at the stigma.

*Fragrancy.*—None.

*Lastingness.*—Each thyrse blooms for about 2 weeks on the plant.

Fruit:

*Type.*—Two-beaked ovoid capsule.

*Color.*—Brown 200D.

Seed:

*Shape.*—Linear.

*Size.*—2 mm. long.

*Color.*—Black 202A.

Pest and Disease Tolerance: Excellent disease resistance to powdery mildew, the common problem of *Heuchera.* Susceptible to *Heuchera* rust and root weevils.

COMPARISON TO SIMILAR *HEUCHERA*

Compared to *Heuchera 'Amber Waves' (U.S. Plant Pat. No.* 13,348) the new variety has a much different leaf color, pale ale to tan to olive green with a heavy silver white veil compared to an amber to olive green tone. The leaves of the new variety are not ruffled.

Compared to the seed parent, *Heuchera* 44-1 (a proprietary unreleased plant), the new variety has pale ale colored foliage rather than light brown and creamy yellow flowers rather than dark pink.

Compared to the pollen parent, *Heuchera* 148-1, (a proprietary unreleased plant), the new variety has creamy yellow flowers rather than white and pale ale colored foliage rather than yellow.

I claim:

1. A new and distinct hybrid of *Heuchera* plant as herein illustrated and described.

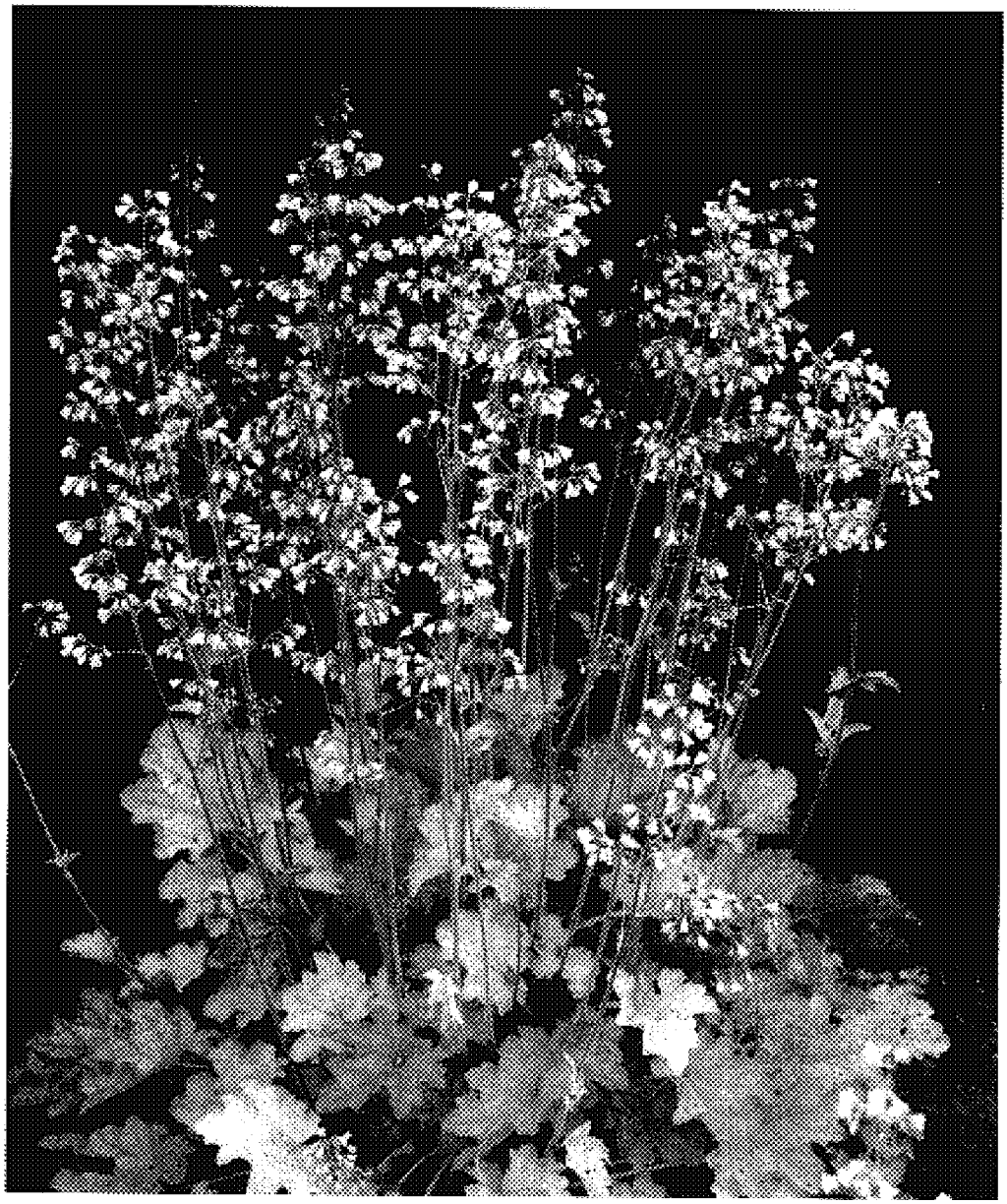

* * * * *